United States Patent [19]

Speaker

[11] Patent Number: 5,284,663
[45] Date of Patent: Feb. 8, 1994

[54] SALT FILM ENCAPSULATED PERFLUOROCARBONS

[75] Inventor: Tully J. Speaker, Philadephia, Pa.

[73] Assignee: Temple University, Philadelphia, Pa.

[21] Appl. No.: 734,461

[22] Filed: Jul. 23, 1991

[51] Int. Cl.$^5$ .............................................. A61K 9/50
[52] U.S. Cl. .................................. 424/489; 424/490; 424/497; 264/4.1
[58] Field of Search ............... 424/450, 457, 489, 490; 264/4.1; 435/283

[56] References Cited

U.S. PATENT DOCUMENTS

| | | | |
|---|---|---|---|
| 3,879,510 | 4/1975 | Kitajima et al. | 424/3 |
| 3,959,457 | 5/1976 | Speaker | 424/469 |
| 3,964,294 | 6/1976 | Shair et al. | 73/53 |
| 4,001,401 | 1/1977 | Bousen | 530/385 |
| 4,107,288 | 8/1978 | Oppenheim et al. | 424/22 |
| 4,133,874 | 1/1979 | Miller et al. | 424/38 |
| 4,376,059 | 3/1983 | Davis et al. | 252/316 |
| 4,425,334 | 1/1984 | Hunt | 424/450 |
| 4,512,762 | 4/1985 | Spears | 604/21 |
| 4,520,109 | 5/1985 | Simmonds et al. | 436/56 |
| 4,675,310 | 6/1987 | Chapman | 514/75 |
| 4,812,445 | 3/1989 | Eden et al. | 514/60 |
| 4,853,370 | 8/1989 | Ecanow et al. | 514/6 |
| 4,917,892 | 4/1990 | Speaker | 424/455 |
| 5,051,353 | 9/1991 | Stratton | 435/2 |
| 5,084,558 | 1/1992 | Rausch | 530/385 |

FOREIGN PATENT DOCUMENTS 0299205 1/1989 European Pat. Off. .

OTHER PUBLICATIONS

"Controlled Release By Using Poly Methacrylic Hydrogels" Journal of Controlled Release, 16, Peppas et al. pp. 203-214, 1991.

"Oil Spill Identification with Microencapsulated Compounds Suitable for Electron Capture" Environmental Science & Technology, 7, No. 2, Mitchell et al. pp. 121-124, 1973.

"Perfluorocarbon Blood Substitutes" CRS Critical Reviews in Oncology Hematology, 6, issue 4, Biro et al., pp. 311-374, 1987.

Synthetic Blood & Medical Technologies Inc. pp. 12, 28, 30, 32, 34, 38, 40 and 42.

Primary Examiner—Paul R. Michl
Assistant Examiner—Raj Bawa
Attorney, Agent, or Firm—Ratner & Prestia

[57] ABSTRACT

An artificial blood substitute comprising Lewis acid—Lewis base salt film microcapsule having a perfluorocarbon encapsulated therein. The Lewis base may be a polyoxyalkylene adduct of an amine and the Lewis acid may be a polyoxyalkylene derivative of a polymeric acid.

12 Claims, No Drawings

SALT FILM ENCAPSULATED PERFLUOROCARBONS

FIELD OF THE INVENTION

This invention relates to a microcapsule composition for the delivery of an oxygen and carbon dioxide carrying compound through the vascular system. In particular, the microencapsulated composition is useful as an artificial blood substitute.

BACKGROUND

A specific type of microcapsulant material and a method of making such material is disclosed in U.S. Pat. No. 3,959,457 (of common assignment and partial common inventorship herewith). This material is comprised of the reaction product produced at the interface boundary of a finely dispersed emulsion, comprising a water immiscible solution of a Lewis base and an aqueous solution of a partially hydrophilic, partially lipophilic Lewis acid.

An improvement in the invention of the '457 patent is disclosed in a presently pending U.S. application (also of common assignment herewith and partial common inventorship), at least one foreign counterpart of the parent of which has been published prior to the conception of the present invention (see European Patent Application, Publication Number 0 299 205, Publication Date, Jan. 18, 1989). According to specific aspects of this prior improvement, polyoxethylene-polyoxypropylene or block copolymers thereof comprise a core-forming adjuvant and/or ethylene oxide adducts of ethylenediamine ("tetronomers") comprise wall-forming adjuvant for use in systems of the '457 patent type. The resultant microcapsules are more robust and more stable physically than the non-adjuvant microcapsules disclosed in the '457 patent.

Perfluorocarbons are known to be useful as blood substitutes but only in the form of dispersions or emulsions. One such known prior art emulsion of perfluorocarbon is marketed under the trade name Fluosol DA. It is understood that this and similar dispersed emulsions exhibit low stability and must be stored at $-40°$ C. Microspheres containing cross-linked hemoglobin and encapsulated hemoglobin have also been prepared for use as a blood substitute. (See U.S. Pat. Nos. 3,875,510 Kitajima et al., 4,133,874 - Miller et al. and 4,376,059 Davis et al.)

Encapsulated fluorocarbons have previously been disclosed as tracers for use in the petroleum and petrochemical fields, but the known encapsulants (see U.S. Pat. Nos. 4,520,109 —Simmonds et al. and 3,964,294 —Shair et al.) are quite different from those used in the present invention.

Heretofore, such perfluorocarbons have been considered poor candidates for encapsulation in systems of the '457 type because their polar character would be expected to destabilize the capsule wall structure.

The extremely low polarity of perfluorocarbons causes them to be incapable of solvating the regions of high charge density associated with ionic centers in systems of the '457 type or of forming hydrogen bonds with water solvating those ionic centers. As a practical result, it has heretofore been impossible to capture perfluorocarbons in charged film microcapsules of the type produced by '457. A technique is described in '457, currently pending U.S. application 07/417,590 and European Patent Application 0 299 205, by which nonpolar materials may be utilized as the dispersed phase and encapsulated. In this technique a solvent of intermediate polarity, such as chloroform, is added to a core material of low polarity, such as light liquid petrolatum, to increase polarity of the dispersed phase. This technique is not applicable to perfluorocarbons because they exhibit such low polarity that they are immiscible with solvents such as chloroform or the even less polar material light liquid petrolatum.

Three other references identified as of possible interest in a patentability search on the present invention are U.S. Pat. Nos. 4,107,288 - Oppenheim et al., 4,512,762 - Spears and 4,812,445 - Eden et al. The first and third of these pertain to encapsulation techniques different from that used in the present invention and the second, at column 2, lines 37-42, makes reference (though negative) to blood exchange with perfluorocarbon chemicals.

BRIEF DESCRIPTION OF THE INVENTION

This invention comprises a microencapsulated perfluorocarbon composition. The invention makes use of a Lewis acid - Lewis base salt microparticulate material similar to that of U.S. Pat. No. 3,959,457, with a polyoxyalkylene adduct of an amine (POAAM), (for example, a polyoxyalkylene adduct of a mono-, di- or polyamine) as the Lewis base reactant or through use of a polyoxyalkylene derivative of a polymeric acid (PODPA), for example, a polyoxyalkylene partial ester of a polymeric acid, as the Lewis acid reactant. More specifically, when said Lewis base is a polyoxyalkylene adduct of an amine, said Lewis acid is a polyacid; when said Lewis acid is a polyoxyalkylene derivative of a polymeric acid, said Lewis base is a simple amine.

In a preferred embodiment, the Lewis base polyoxyalkylene adduct of an amine is a tetrapolyoxyethylene adduct of ethylenediamine, also known as a tetronomer. In another preferred embodiment, the Lewis acid polyoxyalkylene derivative of a polymeric acid is the polyethylene glycol ester of polyacrylic acid in which nominally 30 percent of the carboxyl groups of polyacrylic acid are esterified with the glycol.

Most importantly, a perfluorocarbon (examples of which include perfluorotetralin, perfluorobutylamine and perfluorobutyl ether) is disposed in the core of the microcapsule.

It is believed that the pendant polyethers of the POAAM or of the PODPA provide a layer of moderate polarity interposed between the ionic microcapsule wall and the encapsulated perflurocarbon of low polarity, thus protecting the ionic wall from destabilization by the perfluorocarbon.

Preferably, the microcapsules are of about the same size as or somewhat smaller than red blood cells (i.e. about 3 microns in diameter) so that they can circulate in the vascular system as supplements or replacements for red blood cells, either in a blood substitute or in natural blood. For such purposes, they would ordinarily be combined, in a sterile suspension, with suitable additives, such as physiologic electrolytes and macromolecules contributing to the ionic and osmotic balance required of a blood substitute.

DETAILED DESCRIPTION OF THE INVENTION

Generally, Lewis acid - Lewis base salt film microcapsules, of the type to which this invention is directed, are made as follows:

A solution of a suitable Lewis base in a perfluorocarbon is dispersed in an aqueous solution of a Lewis acid to produce a momentary, finely divided emulsion of perflurocarbon droplets in a continuous aqueous phase. The perfluorocarbon may be, for example, perfluoroalkanes or perfluoroalkenes such as perfluorohexane, perfluoromethylcyclohexane, perfluorodimethylcyclohexane, perfluorotetralin, perfluoromethyltetralin, perfluoromethyldecalin, or perfluoro-5-decene, perfluoroamines such as perfluorotributylamine, perfluoroethers such as perfluorobutyl ether, or halogen substituted perfluorcarbons such as perfluorooctyl bromide.

The Lewis base reactant is selected from a simple amine capable of reacting with a polyoxyalkylene derivative of a polymeric acid and a polyoxyalkylene adduct of a mono-, di-, or poly-amine (POAAM). The POAAM has the following generic structure:

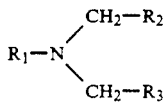

in which, independently,

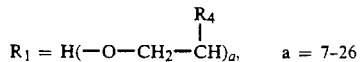

$R_2 = -CH_2-O-R_1$ or $CH_2-N-(R_1)_2$

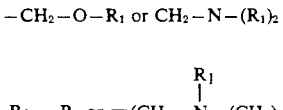

and $R_4 = H$, $CH_3$ or alkyl.

The Lewis acid reactant is selected from a polyacid capable of reacting with a polyoxyalkylene adduct of an amine and a polyoxyalkylene derivative of a polymeric acid (PODPA). The PODPA has the following generic structure:

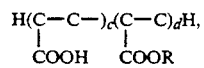

$c = 70-3150$ and $d = 70-1750$ in which c- and d- type repeat units are randomly distributed within the polymer, $c = 70$ to 3150, c-type repeat units comprise from 50–90% of the total polymer, $d = 70$–1750, the sum of $c+d$ is in the range from about 140 to about 3500 and in which:

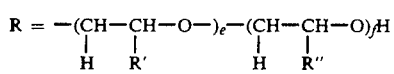

where R' and R'' independently $= H$ or $CH_3$ and $e = 7$ to 75, $f = 7$-75, and the sum of $e+f = 14$ to 85. In the preferred embodiment, c type repeat units comprise approximately 70% of the total polymer, $R'=H$, $e = 14$ and $f = 0$.

For reasons not entirely clear, the general class of POAAM as the Lewis base and the general class of PODPA as the Lewis acid are not well adapted for concurrent use. However, there may be specific compounds having the PODPA and POAAM structures which are capable of producing the microcapsule of the claimed invention. When the Lewis base reactant is a POAAM, the Lewis acid is a polymeric acid capable of reacting with a polyoxyalkylene adduct of an amine, such as acacia, arabic acid, carboxymethylcellulose, ghatti gum, guar gum, polyacrylic acid and the like. As such, the polyacid is not likely to include the polyoxyalkylene derivative of a polymeric acid (PODPA). The preferred concentration range for the Lewis acid is 1%–10% w/v.

Alternatively, in the absence of a POAAM Lewis base, the Lewis acid reactant is a PODPA, and the Lewis base is a simple amine capable of reacting with a polyoxyalkylene derivative of a polymeric acid, a sufficiently strongly basic mono-, di- or poly- amine such as n-hexylamine, octadecylamine, ethylenediamine, piperazine, 2,4-dimethylpentylamine, tetraethylenetriamine, polyethyleneimine and the like. As such, the simple amine is not likely to include the POAAM. The preferred concentration range of the Lewis base is restricted by the limiting solubility of the Lewis base in the perfluorocarbon employed as core material. Typically, the concentration of amine is in the range 0.1 to 10%. While the exact concentration of the solution of amine serving as Lewis base is not critical, it is important to use a total amount of base stoichiometrically equivalent to the non-esterified ionizable carboxylate functions of the PODPA.

In accordance with the present invention, the Lewis base is dissolved in the perfluorocarbon (PFC) resulting in a PFC-Lewis Base (PFC-LB) phase. The Lewis acid is dissolved in the aqueous solution, prior to combining the aqueous solution with the PFC-LB phase. A momentary, finely dispersed emulsion of PFC droplets in a continuous aqueous phase is produced with rapid stirring. The Lewis acid and Lewis base must be substantially soluble in the appropriate phase. Accordingly, in one of the preferred embodiments, the Lewis base, a POAAM, is dissolved in the PFC phase, and arabic acid is dissolved in the aqueous phase. In the other preferred embodiment, the Lewis base 2,4-dimethylpentylamine is dissolved in the PFC phase and the Lewis acid, a PODPA, is dissolved in the aqueous phase.

In the present invention, perfluorocarbon encapsulation efficiencies near 60% are easily achieved with a 1:1 ratio of aqueous (Lewis acid-containing) phase to nonaqueous (Lewis base-PFC-containing) phase, essentially 100% of the perfluorocarbon may be encapsulated if the initial nonaqueous to aqueous phase ratio is adjusted to 2:5.

GENERAL PROCEDURES FOR FORMING MICROCAPSULES

In all instances where an aqueous solution is utilized as the continuous phase for the dispersion of the PFC-Lewis base, it is preferred, but not essential, that the PFC-Lewis base be slowly and steadily added to the aqueous solution over a period of approximately 30 seconds. Generally, solutions are prepared and reactions take place at room temperature, unless otherwise stated. Any of several means to disperse the PFC-Lewis base in the aqueous medium may be employed including:

a. vigorously stirring the solution with a magnetically driven stirring bar at a nominal shear rate, generally 700 or more cm/s;
b. vigorously mixing the solution with a multi-orifice axial turbine (such as a Brinkmann homogenizer PT10/35 and generator PST/10, Brinkmann Instruments, Westbury, N.Y.) at a nominal setting of 5; or
c. vigorously agitating the solutions with an ultrasonic probe (such a Heat Systems model W185D, Ultrasonics, Inc., Plainview, N.Y.) at a nominal output of 100 watts.

GENERAL METHOD OF PREPARING A MICROENCAPSULATED PERFLUOROCARBON

A 10 ml volume of a 10% w/v aqueous solution of arabic acid was mixed with a stoichiometrically equivalent solution of a tetronomer, (i.e., ca 2.2 g), such as Tetronic 702 product of BASF-Wyandotte Corp., Wyandotte, Mich., 5 ml of perfluorotetralin. The mixture was insonated at 20 kilohertz for 1-5 minutes at a power output of about 100 watts. The sonic energy dispersed the perfluorocarbon phase into small droplets which had the momentary characteristic of an emulsion stabilized in part by the surfactant properties of arabic acid. Studies with small volume (2-5 ml) formulations insonation produces finer dispersions but does not appear to markedly increase encapsulation efficiency.

The reaction mixture was centrifuged (10,000 gravity minutes) and the supernatant removed. Distilled water was added and the pellet of microcapsules was resuspended by vortexing. The suspension was allowed to stand a few minutes to permit unencapsulated perfluorocarbon phase to separate, and the microcapsular suspension was harvested. The microcapsules were resuspended in distilled water and centrifuged as needed to remove unreacted manufacturing components. The washed product was rendered as a flowable concentrate by a final centrifugation. The resulting preparation of microencapsulated perfluorocarbon is stable at 20° C. for about one month.

Similar experiments were conducted to compare the encapsulation of perfluorocarbons with different Lewis acids. As set forth in Table I below, the control 1, polyethylene glycol alone is not capable of encapsulating perfluorocarbon nor does control 2, polyacrylic acid alone, or control 3, the simple non-esterified combination of polyethylene glycol mixed with polyacrylic acid encapsulate perfluorocarbon, in an attempted wall forming reaction using 2,4-dimethylpentamine as Lewis base.

In contrast, experiment 4, using polyacrylic acid (ca 30%) esterified with polyethylene glycol as the Lewis acid and the same 2,4-dimethylpentamine as Lewis base does effectively 100% encapsulate perfluorocarbon.

TABLE I

| Components | Controls 1 | 2 | 3 | Experiment 4 |
|---|---|---|---|---|
| PEG | 300 mg | 0 | 300 mg | 0 |
| PAA | 0 | 126 mg | 126 mg | 0 |
| PEGPA | 0 | 0 | 0 | 400 mg |
| AMINE | 192 mg | 192 mg | 192 mg | 131 mg |
| AQ | 10 mL | 10 mL | 10 mL | 10 mL |
| PFC | 4 mL | 4 mL | 4 mL | 4 mL |
| ucaps | no | no | no | yes |
| ave d (u) | 0 | 0 | 0 | <2 |
| % encap | 0 | 0 | 0 | 100 | where
PEG = polyethylene glycol 600 (ave MW = 600)
PAA = polyacrylic acid (ave MW = 250000, mEqWT = 72 mg)
POGPA = polyethylene glycol 600 polyacrylate (degree of esterification: ca 30%, mEqWt = 350 mg)
AMINE = 2,4-dimethylpentylamine (MW = 115, mEqWt = 115 mg)
AQ = distilled water
PFC = perfluorcarbon (perfluorodec-5-ene)

Additives such as physiologic electrolytes and macromolecules may be incorporated in the microencapsulated perfluorocarbon suspension. These additives contribute to and adjust for the ionic and osmotic balance required of a blood substitute, whose serum specifications are well known, or a perfusion fluid.

The microencapsulated perfluorocarbon is stable at room temperature. It should be capable of circulating freely in the vascular system; taking up, carrying and releasing dissolved oxygen to tissues; and capturing carbon dioxide from tissues and releasing the lungs.

It is believed that the material of the present invention will be useful as (or in) perfusion fluids in hospital surgical suites, and as (or in) a temporary substitute or replacement for human blood, for example, when supplies of real human blood are limited or unavailable, when inadequate time or facility is available to determine the blood type of the intended recipient, such as at sites of accidents, disasters, catastrophe scenes, battlefields and hospital emergency rooms; when there is concern for transmission of blood-borne diseases, such as AIDS and hepatitis, from donor to recipient; when the use of human blood is rejected for religious or ethical reasons. The microencapsulated perfluorocarbons of this invention may also benefit athletes, marathon runners for example, anemics, and animals, such as race horses, by providing a means to improve the oxygen and carbon dioxide exchange capacity of the vascular system of such subjects.

Problems with other known perfluorocarbons used as artificial blood are overcome by the present invention, including stability problems, as the microencapsulated perfluorocarbons of the present invention are stable, and do not coalesce, at 20° C. for about one month. The microencapsulated perfluorocarbon of the present invention eliminates the need for thawing the blood substitute and oxygenating the perfluorocarbon prior to administration. Furthermore, the microencapsulated perfluorocarbon of the invention eliminates the need for blood typing prior to use. Accordingly, the microencapsulated perfluorocarbon of the claimed invention may be used more rapidly than conventional blood substitutes.

In addition to use as a blood substitute or a perfusion fluid, the microencapsulated perfluorocarbon of the present invention also has utility in other applications in which stable compositions including perfluorocarbons have been shown to be useful, such as a contrast agent in medical imaging. Perfluorocarbon-containing perfusion fluid may also be used during surgery and for wound healing to increase oxygen carrying capacity to damaged and surrounding tissues.

While this invention has been disclosed with reference to specific embodiments, it is apparent that other embodiments and equivalent variations of this invention may be devised by those skilled in the art without departing from the true spirit and scope of this invention. The appended claims are intended to be construed to include all such embodiments and equivalent variations.

What is claimed is:

1. A Lewis acid-Lewis base salt film microcapsule having a microcapsule wall and perfluorocarbon as a core, wherein said Lewis acid is selected from the group consisting of arabic acid, acacia gum, carboxymethylcellulose, ghatti gum, guar gum and a polyoxyalkylene derivative of a polymeric acid having the structure $$H(\underset{COOH}{C-C})_c(\underset{COOR}{C-C})_d H$$

in which c- and d-type repeat units are randomly distributed within the polymers, $c=70$ to 3150, c-type repeat units consist essentially of from 50-90% of the total polymer, $d=70-1750$, the sum of $c+d$ is in the range from about 140 to about 3500 and in which:

$$R = -(\underset{H}{\underset{|}{CH}}-\underset{R'}{\underset{|}{CH}}-O-)_e-(\underset{H}{\underset{|}{CH}}-\underset{R''}{\underset{|}{CH}}-O)_f H$$

where
R' and R'' independently $=H$ or $CH_3$ and $e=7-75$, $f=7-75$, and the sum of $e+f=14$ to 85, and
said Lewis base is a simple amine selected from the group consisting of n-hexylamine, 2,4-dimethylpentylamine, octadecylamine, ethylenediamine, piperazine, tetraethylenetriamine and polyethyleneimine and a polyoxyalkylene adduct of an amine having the structure $$R_1-N\begin{matrix}CH_2-R_2\\ \\ CH_2-R_3\end{matrix}$$

in which, independently, $$R_1 = H(-O-CH_2-\overset{R_4}{\underset{|}{CH}})_a, \quad a = 7-26$$

$R_2 = -CH_2-O-R_1$ or $CH_2-N-(R_1)_2$ $$R_3 = R_2 \text{ or } -(CH_2-\overset{R_1}{\underset{|}{N}}-(CH_2)_b-R_2, \quad b = 7-26$$

and
$R_4=H$, $CH_3$ or alkyl,
wherein when said Lewis base is a polyoxyalkylene adduct of an amine said Lewis acid is selected from the group consisting of arabic acid, acacia gum, carboxymethylcellulose, ghatti gum and guar gum, and when said Lewis acid is a polyoxyalkylene derivative of a polymeric acid said Lewis base is selected from the group consisting of n-hexylamine, 2,4-dimethylpentylamine, octadecylamine, ethylenediamine, piperazine, tetraethylenetriamine and polyethyleneimine, and
wherein said Lewis acid is in a concentration of 1-10% weight by volume and said Lewis base is in a stoichiometric amount sufficient to form a neutral salt film.

2. A microcapsule of claim 1 wherein said perfluorocarbon is selected from the group consisting of perfluoroalkanes, perfluorocycloalkanes, perfluoroalkenes, perfluoroamines, perfluoroethers, and halogen substituted perfluorocarbons.

3. A microcapsule of claim 2 wherein said perfluorocarbon is selected from the group consisting of perfluorotetralin, perfluoromethyldecalin, perfluorohexane, perfluoromethylcyclohexane, and perfluoro-1,3-dimethylcyclohexane.

4. A microcapsule of claim 2 wherein said perfluorocarbon is perfluorotributylamine.

5. A microcapsule of claim 2 wherein said perfluorocarbon is perfluorobutyl ether.

6. A microcapsule of claim 2 wherein said perfluorocarbon is perfluorooctyl bromide.

7. A microcapsule of claim 1 wherein said polyacid is arabic acid.

8. A microcapsule of claim 7 wherein said polyoxyalkene adduct of an amine is a polyoxyethylene adduct of ethylenediamine.

9. A microcapsule of claim 1 wherein said polyoxyalkene adduct of an amine has polyoxyalkylene chains disposed between said microcapsule wall and said core.

10. In a blood substitute, the improvement consisting essentially of, as an artifical red blood cell, a Lewis acid-Lewis base salt film microcapsule having a microcapsule wall and perfluorocarbon as a core
wherein said Lewis acid is as recited in claim 1 and said Lewis base is as recited in claim 1,
wherein when said Lewis base is a polyoxyalkylene adduct of an amine said Lewis acid is selected from the group consisting of arabic acid, acacia gum, carboxymethylcellulose, ghatti gum and guar gum, and when said Lewis acid is a polyoxyalkylene derivative of a polymeric acid said Lewis base is selected from the group consisting of n-hexylamine, 2,4-dimethylpentylamine, octadecylamine, ethylenediamine, piperazine, tetraethylenetriamine and polyethyleneimine, and
wherein said Lewis acid is in a concentration of 1-10% weight by volume and said Lewis base is in a stoichiometric amount sufficient to form a neutral salt film.

11. In a perfusion fluid, the improvement consisting essentially of, as an artifical red blood cell, a Lewis acid-Lewis base salt film microcapsule having a microcapsule wall and perfluorocarbon as a core
wherein said Lewis acid is as recited in claim 1 and said Lewis base is as recited in claim 1,
wherein when said Lewis base is a polyoxyalkylene adduct of an amine said Lewis acid is selected from the group consisting of arabic acid, acacia gum, carboxymethylcellulose, ghatti gum and guar gum, and when said Lewis acid is a polyoxyalkylene derivative of a polymeric acid said Lewis base is selected from the group consisting of n-hexylamine, 2,4-dimethylpentylamine, octadecylamine, ethylenediamine, piperazine, tetraethylenetriamine and polyethyleneimine, and
wherein said Lewis acid is in a concentration of 1-10% weight by volume and said Lewis base is in a stoichiometric amount sufficient to form a neutral salt film.

12. A method of making a microencapsulated perfluorocarbon having a wall and a core, consisting essentially of combining:

a. an aqueous phase including a Lewis acid wherein said Lewis acid is selected from the group consisting of arabic acid, acacia gum carboxymethylcellulose, ghatti gum, guar gum, and a polyoxyalkylene derivative of a polymeric acid having the structure $$H(C-C)_c(C-C)_dH$$
$$\phantom{H(}|\phantom{C-C)_c}|$$
$$\phantom{H(}COOH\phantom{C)_c}COOR$$

in which c- and d-type repeat units are randomly distributed within the polymer, $c = 70$ to 3150, c-type repeat units consist essentially of from 50–90% of the total polymer, $d = 70$ to 1750, the sum of $c+d$ is the range from about 140 to 3500 and in which:

$$R = -(CH-CH-O-)_e-(CH-CH-O)_fH$$
$$\phantom{R=-(}|\phantom{H-CH}|\phantom{-O-)_e-(}|\phantom{H-CH}|$$
$$\phantom{R=-(}H\phantom{-C}R'\phantom{H-O-)_e-(}H\phantom{-C}R''$$

where
$R'$ and $R''$ independently $= H$ or $CH_3$ and $e = 7$–75, $f = 7$–75, and the sum of $e+f = 14$ to 85, with b. a non-aqueous phase including
  (1) a stoichiometric equivalent of a Lewis base,
  wherein said Lewis base is selected from the group consisting of n-hexylamine, 2,4-dimethylpentylamine, octadecylamine, ethylenediamine, piperazine, tetraethylenetriamine and polyethyleneimine, and a polyoxyethylene adduct of an amine having the structure $$R_1-N\begin{array}{c}CH_2-R_2\\CH_2-R_3\end{array}$$

in which, independently, $$R_1 = H(-O-CH_2-\overset{R_4}{\underset{|}{CH}})_a, \quad a = 7\text{-}26$$

$$R_2 = -CH_2-O-R_1 \text{ or } CH_2-N-(R_1)_2$$

$$R_3 = R_2 \text{ or } -(CH_2-\overset{R_1}{\underset{|}{N}}-(CH_2)_b-R_2, \quad b = 7\text{-}26$$

and
$R_4 = H$, $CH_3$ or alkyl,
and,
wherein said Lewis acid is in a concentration of 1–10% weight by volume and said Lewis base is in a stoichiometric amount sufficient to form a neutral salt film,
  (2) a perfluorcarbon selected from the group consisting of perfluoroalkanes, perfluorocycloalkanes, perfluoroalkenes, perfluoroamines, perfluoroethers, and halogen substituted perfluorocarbons;

c. dispersing said aqueous and said non-aqueous phases together to form an emulsion, wherein said perfluorocarbon is disposed in said core.

* * * * *

UNITED STATES PATENT AND TRADEMARK OFFICE
CERTIFICATE OF CORRECTION

PATENT NO. : 5,284,663
DATED : February 8, 1994
INVENTOR(S) : Tully J. Speaker

It is certified that error appears in the above-indentified patent and that said Letters Patent is hereby corrected as shown below:

Column 7, line 19, delete "polymers" and insert therefor --polymer--.

Signed and Sealed this

Ninth Day of August, 1994

Attest:

BRUCE LEHMAN

Attesting Officer     Commissioner of Patents and Trademarks